US006639965B1

(12) United States Patent
Hsieh et al.

(10) Patent No.: US 6,639,965 B1
(45) Date of Patent: Oct. 28, 2003

(54) METHODS AND APPARATUS FOR CARDIAC IMAGING WITH CONVENTIONAL COMPUTED TOMOGRAPHY

(75) Inventors: Jiang Hsieh; Tin-Su Pan, both of Brookfield, WI (US); Yun Shen, Tokyo (JP); Steve John Woloschek, Franklin, WI (US); Mark E. Woodford, Waukesha, WI (US); Kishore C. Acharya, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/410,157

(22) Filed: Sep. 30, 1999

(51) Int. Cl.[7] .................................................. A61B 6/00
(52) U.S. Cl. ............................................. 378/8; 378/15
(58) Field of Search ...................... 378/8, 4, 15, 39, 378/95

(56) References Cited

U.S. PATENT DOCUMENTS

| | | | |
|---|---|---|---|
| 3,952,201 A | | 4/1976 | Hounsfield |
| 4,182,311 A | * | 1/1980 | Seppi et al. ................ 128/653 |
| 4,530,109 A | | 7/1985 | Klausz |
| 4,641,328 A | | 2/1987 | Fujise |
| 4,868,747 A | | 9/1989 | Mori et al. |
| 4,994,965 A | * | 2/1991 | Crawford et al. ...... 364/413.15 |
| 5,216,601 A | * | 6/1993 | Crawford et al. ............. 378/14 |
| 5,271,055 A | | 12/1993 | Hsieh et al. |
| 5,383,231 A | * | 1/1995 | Yamagishi ................... 378/15 |
| 5,533,085 A | | 7/1996 | Sheehan et al. |
| 5,544,212 A | | 8/1996 | Heuscher |
| 5,602,891 A | | 2/1997 | Pearlman |
| 5,751,782 A | * | 5/1998 | Yoshitome ................. 378/98.5 |
| 5,832,051 A | * | 11/1998 | Lutz ............................... 378/8 |
| 5,892,051 A | * | 11/1998 | Lutz ............................... 378/8 |
| 5,848,117 A | * | 12/1998 | Urchuk et al. ................ 378/19 |
| 6,154,516 A | | 11/2000 | Heuscher et al. |

FOREIGN PATENT DOCUMENTS

| | | |
|---|---|---|
| DE | 197 40 124 A1 | 4/1999 |
| EP | 0 370 341 A2 | 5/1990 |
| EP | 1 013 225 A1 | 6/2000 |
| EP | 1 050 272 A1 | 11/2000 |
| EP | 1 072 224 A2 | 1/2001 |
| WO | WO 00/30539 | 6/2000 |

OTHER PUBLICATIONS

European Search Report dated Sep. 17, 2001, for European Patent Application No. EP 00 30 8616, for General Electric Company.

Woodhouse et al., "Coronary Arteries: Retrospective Cardiac Gating Technique to Reduce Cardiac Motion Artifact at Spiral CT," Radiology, Aug. 1997, pp. 566–569.

Spraggins et al., "Retrospective Cardiac Gating Requiring No Physiological Monitoring," undated, one page.

Broderick et al., "Measurement of Coronary Artery Calcium with Dual–Slice Helical CT Compared with Coronary Angiography: Evluation of CT Scoring Methods, Interobserver Variations, and Reproducibility," AJR: 167, Aug. 1996, pp. 439–444.

* cited by examiner

Primary Examiner—Drew A. Dunn
Assistant Examiner—Hoon K. Song
(74) Attorney, Agent, or Firm—Carl B. Horton, Esq.; Armstrong Teasdale LLP

(57) ABSTRACT

A method and apparatus for imaging a heart with a scanning computed tomography (CT) imaging system. A cardiac cycle of a patient is measured. The patient's heart is then scanned with the scanning CT imaging system at an angular rate asynchronous to the measured cardiac cycle to obtain image data. An image of the patient's heart is then assembled from chronologically discontinuous segments of the image data. The image is representative of a selected portion of the cardiac cycle.

50 Claims, 5 Drawing Sheets

METHODS AND APPARATUS FOR CARDIAC IMAGING WITH CONVENTIONAL COMPUTED TOMOGRAPHY

BACKGROUND OF THE INVENTION

This invention relates generally to methods and apparatus for cardiac CT imaging, and more particularly to methods and apparatus for reducing induced motion artifacts in cardiac CT imaging.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In one known CT scanner, the rotating gantry rotates at a rate no greater than 2.0 rotations per second, or equivalently, 0.5 seconds per rotation. A typical period for a cardiac cycle is slightly less than one second. Thus, a patient's heart goes through a substantial portion of its cycle during one gantry revolution. Motion-induced image artifacts result and are a major problem in cardiac CT imaging. In one known system, to reduce artifacts to an acceptable level, an entire scan is performed in a fraction of cardiac cycle with an electron beam CT (EBCT) imaging device. In an EBCT imaging device, x-ray emissions generated by a scanning electron beam are used for imaging. Physical rotation of a gantry is eliminated, and a scan of the electron beam can be completed in as little as 50 milliseconds to essentially completely freeze cardiac motion for coronary imaging. However, EBCT imaging devices remain considerably more expensive than conventional CT imaging devices and are not available in many hospitals. It would therefore be desirable to provide methods and apparatus for reducing motion-induced artifacts in cardiac imaging with conventional CT imaging equipment, or with conventional CT imaging equipment having only inexpensive modifications.

BRIEF SUMMARY OF THE INVENTION

The present invention thus provides methods and apparatus for reducing motion-induced artifacts in CT imaging equipment, including those with a conventional rotating gantry, radiation source, and radiation detector array. For example, in one embodiment, a method for imaging a heart with a scanning computed tomography (CT) imaging system is provided in which a cardiac cycle of a patient is measured; the patient's heart is scanned with the scanning CT imaging system, at an angular rate asynchronous to the measured cardiac cycle to obtain image data; and an image of the patient's heart is assembled from chronologically discontinuous segments of the image data. The assembled image is representative of a selected portion of the cardiac cycle, for example, a relatively quiescent portion.

The above-described embodiment provides greatly improved temporal resolution, because a complete data set can be formed from chronologically discontinuous segments of image data that are each obtained during a very short period of time and at equivalent phases of the patient's cardiac cycle. No special gantry, radiation source, or detector array is required for the CT scanning equipment, yet temporal resolutions comparable to those obtainable with EBCT imaging devices is attainable. The resulting images are useful in medical applications requiring high temporal resolution images, for example, calcification scoring, which requires a high-resolution image of a relatively still heart.

DETAILED DESCRIPTION OF THE INVENTION

Figure 1:
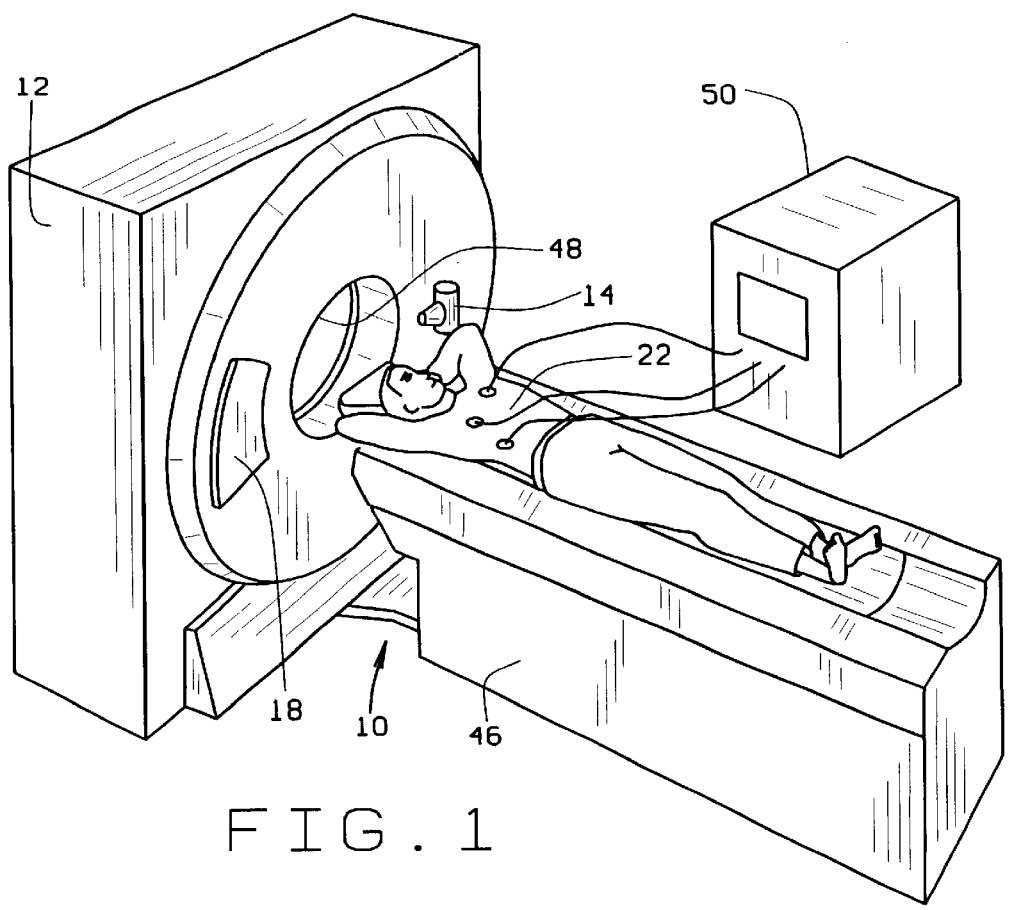
FIG. 1 is a pictorial view of a CT imaging system.
Figure 2:
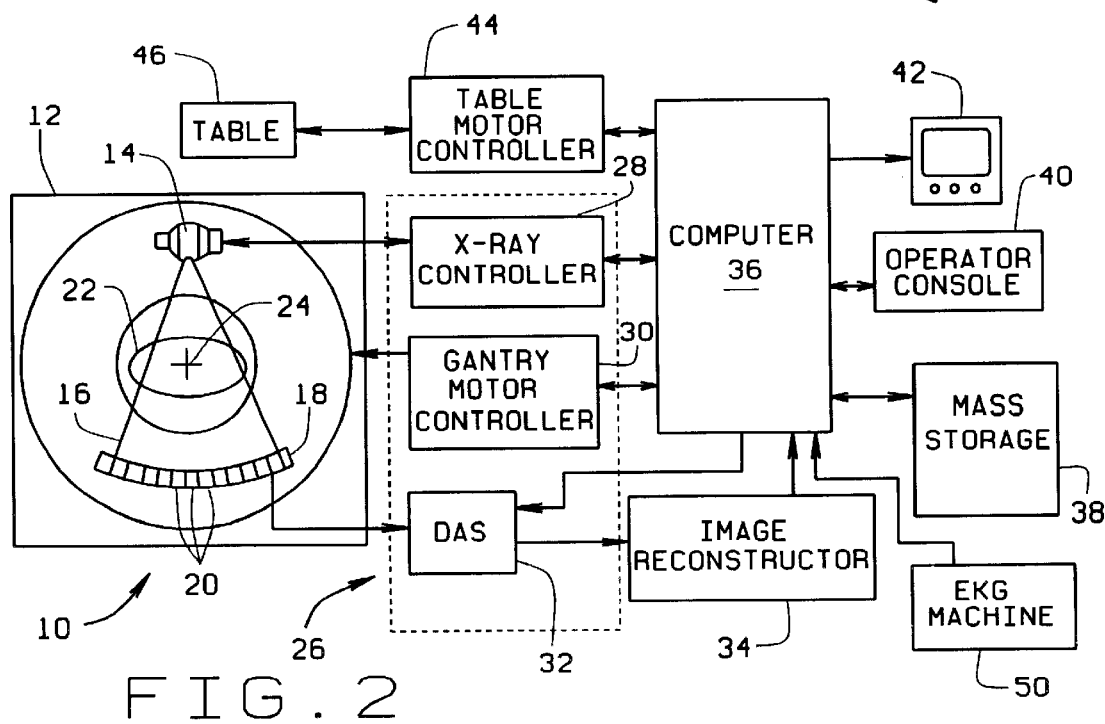
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48 along an axis of rotation of gantry 12, i.e., along a z-axis.

In one embodiment, CT imaging system 10 provides significantly improved temporal resolution by scanning the heart of patient 22 at an angular rate asynchronous to a measured cardiac cycle to obtain imaging data. An image of the heart of patient 22 at a selected portion of the cardiac cycle is then reassembled from chronologically discontinuous segments of image data.

Figure 3:
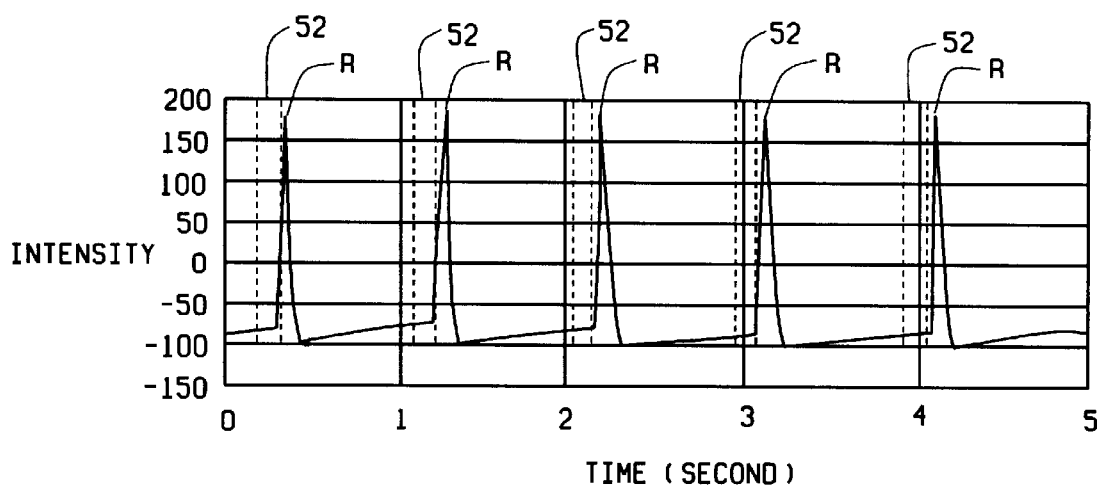
FIG. 3 is a graph illustrative of segments of image data obtained in one embodiment of the present invention, relative to phases of a cardiac cycle of a patient.

An EKG machine 50 is used to obtain an EKG recording of patient 22 immediately before scanning with imaging system 10. It is assumed that an EKG obtained at this time, such as that shown in FIG. 3, is adequately representative of a heart rate of patient 22 during a scan. Peaks R, which are nearly one second apart, are preceded by a relatively quiescent period 52 of the cardiac cycle of patient 22. Because the heart is relatively still during this portion of the cycle, this is the most advantageous portion for providing images with a minimum of motion-induced artifacts. Quiescent period 52 is also selected for imaging in at least one known diagnostic test in which cardiac calcification deposits are scored.

Quiescent period 52 is too short to provide a satisfactory image of the heart when gantry 12 completes a full 360° rotation every 0.5 seconds. Therefore, image data is collected, one during each successive quiescent period 52 during a plurality of gantry rotations, each time at gantry positions providing segments having different view angles. To obtain a satisfactory image, in one embodiment, data from segments that, in total, correspond to a scan of 180° plus a fan angle of data is accumulated over five cardiac cycles. As used herein, a fan angle is defined as an angle of fan-shaped radiation beam 16 intercepted by detector array 18.

In one known CT scanner in which gantry 12 completes a full rotation in 0.5 seconds, a total amount of image data corresponding to 180° plus one fan angle is collected in 0.3 seconds. Five segments totaling this amount of image data are collected during quiescent period 52. Each segment represents data collected in a 60 millisecond window, and each segment is representative of only a portion of a total scan of 180° plus one fan angle. However, the five segments are of adjacent angular ranges, so that, when assembled, a total scan of 180° plus one fan angle is produced.

Each 60 millisecond window occurs during a different rotational cycle of gantry 12, but at a corresponding portion of a cardiac cycle. By assembling 60 millisecond slices of data obtained in this manner, a significant improvement in temporal response of imaging system 10 is achieved. Resulting image resolution approaches that of an EBCT scanner.

Different numbers of image segments, for example, four, eight, or ten, can be collected, depending upon the rate of rotation of gantry 12 and a cardiac cycle of patient 22. Cardiac cycle time of the heart of patient 22 is measured, and a rotation rate of gantry 12 is set that is asynchronous with the measured cardiac cycle time. An asynchronous gantry rotation rate is selected to ensure that image data obtained during multiple segments represent essentially non-overlapping or only slightly overlapping angular portions of a total assembled scan. For example, if a measured heart rate is 60 beats per minute (bpm), a rate of 1.0 rotations per second would be unsatisfactory, because gantry 12 would be at the same angle during identical phases of the cardiac cycle. For one known CT scanner for which speeds of 1.0, 0.8, 0.7, 0.6 and 0.5 seconds per gantry rotation are available, the following table can be used as a guideline for satisfactory scan rate selection.

TABLE I

| Heart rate (bpm) | 60–65 | 65–75 | 70–88 | 89–100 |
|---|---|---|---|---|
| gantry rate (sec/rotat.) | 0.8 | 0.7 | 0.6 | 0.5 |

In one embodiment, data acquisition is accomplished in an axial mode. Table 46, on which patient 22 rests, remains stationary during multiple gantry 12 rotations, for example, five rotations, during which a set of chronologically discontinuous image data to be assembled is collected. After the image data is collected, table 46 is indexed or stepped in a z-axis direction to another location if additional slices of data are to be collected. In one embodiment, scanner 10 is a multi-slice scanner, and table 46 indexes or steps a distance dependent upon volume coverage. For example, if four 2.5 mm data slices are obtained during axial scans, table 46 indexes 10 mm (=4 slices×2.5 mm) so that consecutive scans from which separate images are assembled are of non-overlapping volumes. This index size is equal to volume coverage of data in the previous scan. In another embodiment, a larger index or step size is used when images of contiguous volumes are not required.

In one embodiment, data acquisition is accomplished in a helical scan mode, so that table 46 advances during scanning along a z-axis. A helical pitch is selected in accordance with a number of segments desired for image reconstruction and a selected z-axis location for all segments. For example, CT scanner 10 operates in four-slice mode, and eight segments are desired to form a complete data set. In this example, a helical pitch of 0.5:1 is used so that the same z-axis slice location is viewed eight times during data acquisition. In another embodiment, helical pitch is optimized for sampling continuity. For example, scanner 10 operates in four-slice mode, and helical pitch of 5/6:1 is used to ensure that each segment starts at the same z-axis location for a heart rate of 64.3 bpm and a scan speed of 0.8 sec. As another example, a helical pitch of 1:1 is used to ensure that the z-axis location for neighboring views in adjacent segments has substantially the same z-location, to ensure continuity of the projection data set.

Figure 4:
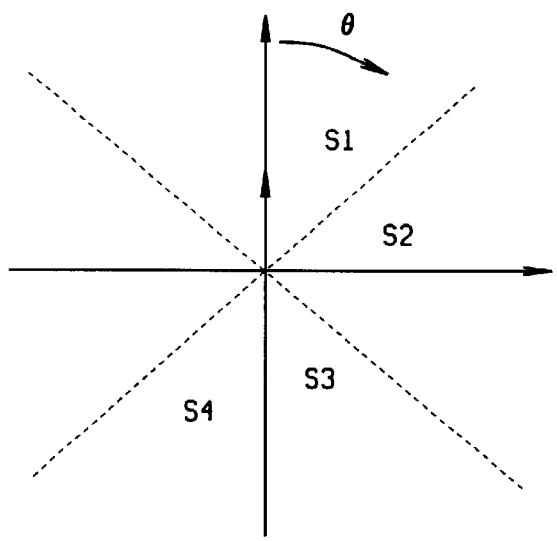
FIG. 4 is a chart illustrative of chronologically discontinuous segments of image data obtained sequentially one embodiment of the invention.
Figure 5:
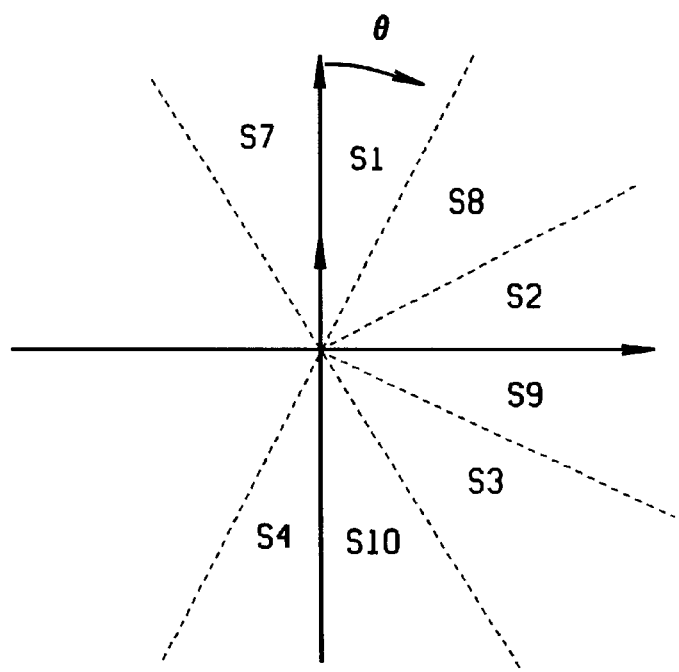
FIG. 5 is a chart illustrative of segments of shuffled, chronologically discontinuous image data obtained in another embodiment of the invention.

In one embodiment, chronologically discontinuous segments of a projection are acquired in sequential order, i.e., segments of data representative of each next adjacent view angle range are obtained sequentially. Referring to the example illustrated in FIG. 4, four segments are obtained of a 65 beat/second cardiac cycle with a gantry 12 rotation rate of 0.8 seconds/revolution. Gantry 12 rotates in a θ direction. Each segment S1, S2, S3, and S4 is obtained, in the order indicated by their numbering, in a 123 millisecond portion of consecutive cardiac cycles. In another embodiment, "shuffled" segments of a projection are acquired, i.e., segments of data representative of next adjacent view angle ranges are obtained nonsequentially. For example, referring to FIG. 5, eight segments are obtained of a 65 beat/second cardiac cycle are acquired with a gantry 12 rotation rate of 0.8 seconds/revolution. Each segment S1, S2, S3, S4, S5, S6, S7, and S8 is obtained in the order indicated by their numbering in separate 61.5 millisecond periods of consecutive cardiac cycles. However, as shown in FIG. 5, consecutively obtained segments are not immediately adjacent one another. Instead, they are obtained in a "shuffled" order and are assembled according to the view angle ranges from which they are obtained, as shown in FIG. 5.

Figure 6:
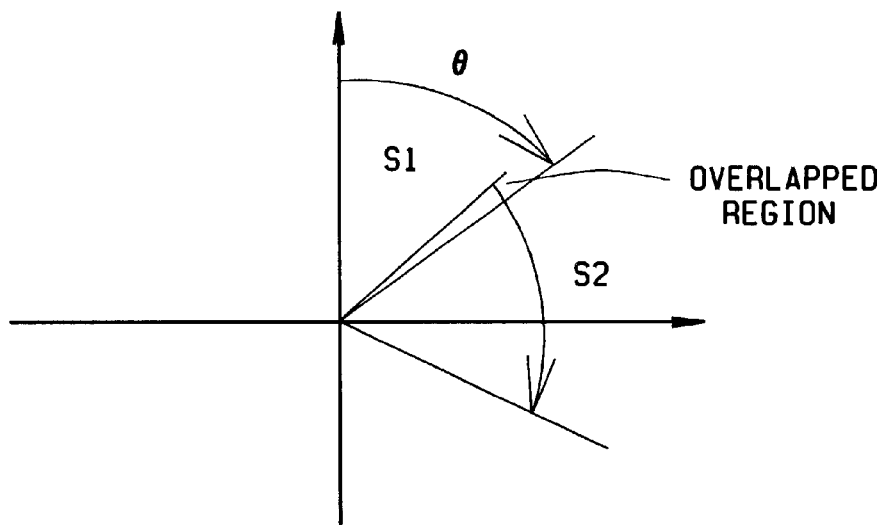
FIG. 6 is a chart illustrative of overlapping of image data segments.
Figure 7:
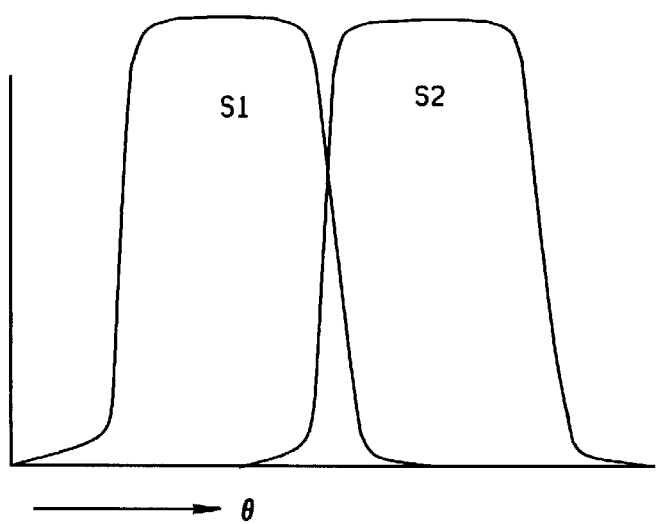
FIG. 7 is a chart showing blending of adjacent, overlapping image data segments.

In one embodiment, to avoid discontinuity between boundaries of adjacent segments, segments are blended prior to image reconstruction. For example, adjoining segments S1 and S2 are obtained from slightly overlapping view angle ranges, as shown in FIG. 6, and a weighting function is applied segments S1 and S2 as a function of view angle, as shown in FIG. 7. The weighting functions of overlapping segments sum to unity at each angular position at which they overlap. Once the projections are blended, artifact-free images are obtained by applying an appropriate additional weighting. For example, in one embodiment in which projection data is acquired over a 220° angular range, a known halfscan weighting function is used. In one embodiment in which projection data is obtained over a complete 360° angular range, another weighting function, for example, a known helical scan weighting such as HE or HI weighting, or an underscan weighting function is used.

Figure 8:
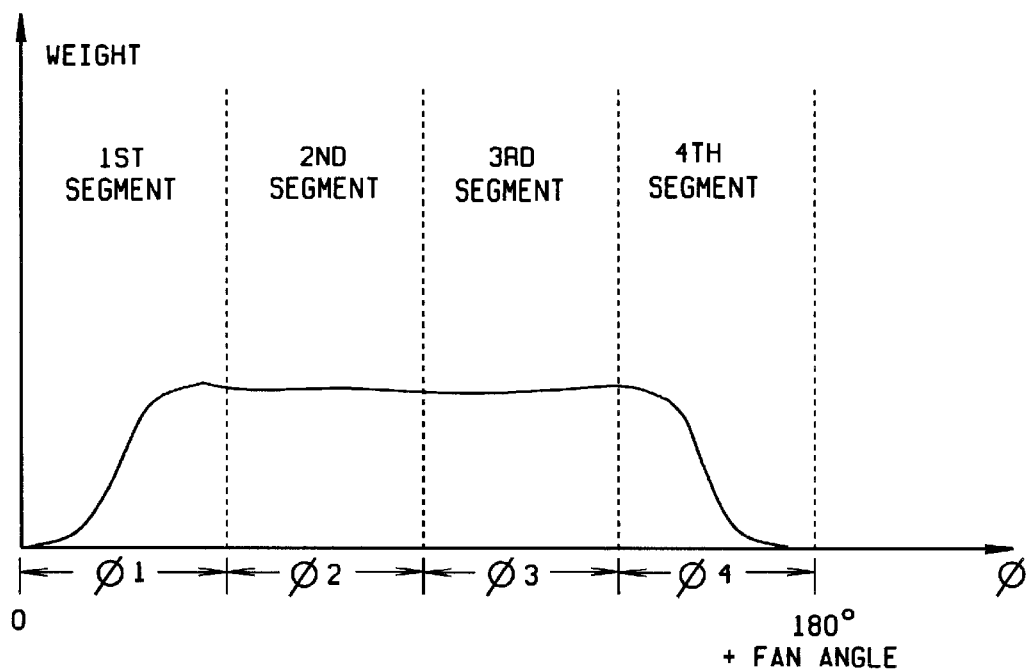
FIG. 8 is a graph showing a weighted scan of 180° plus one fan angle divided into four equal segments for scanning, so that the first and last segments have substantially better resolution than the middle two segments.

Because of applied weighting functions, an effective temporal resolution for segments is no longer constant. For example, in an embodiment in which a half-scan weight is used and the 180° plus fan angle range is evenly divided into 4 segments, the first and last segments have substantially better resolution than the middle two segments. FIG. 8 shows weights for an isochannel as a function of projection angle. Note that weights for an initial portion of the 1st segment and a final portion of the 4th segment are substantially zero. Therefore, their contribution to final image formation is small. As a result, temporal resolution for these two segments is substantially better than that of the others.

Figure 9:
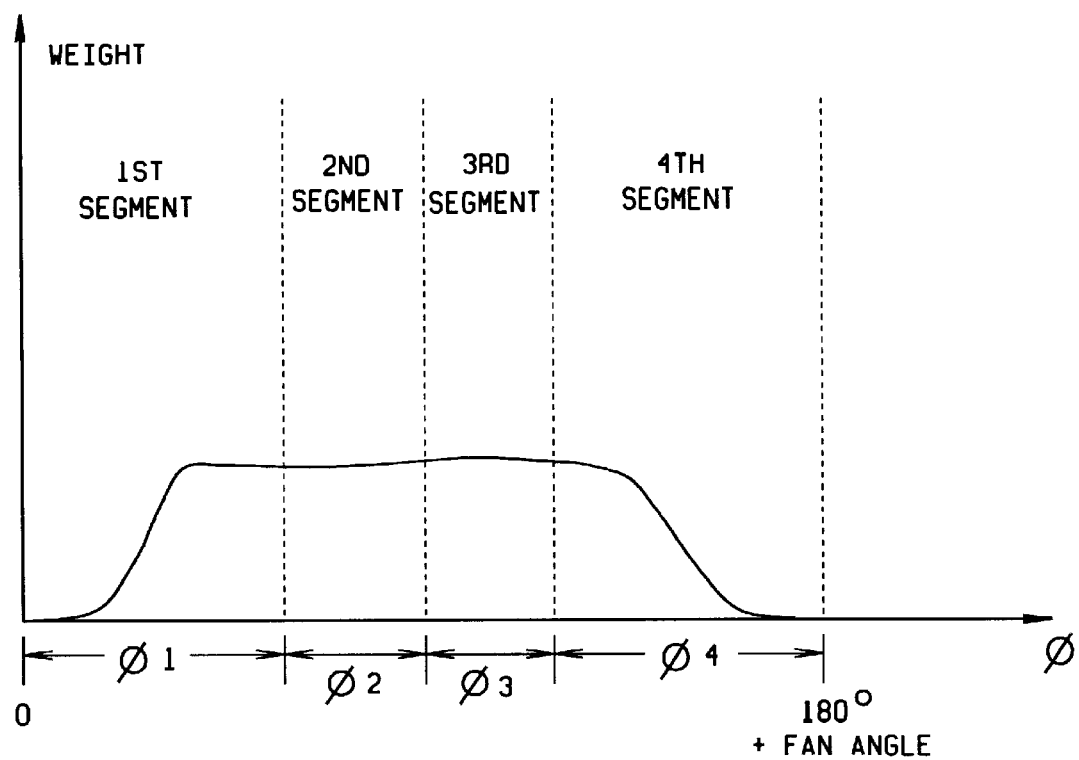
FIG. 9 is a graph showing a weighted scan of 180° plus one fan angle divided into unequal segments for scanning, to equalize temporal resolution of the segments after weighting is applied.

Overall system temporal resolution, however, is determined by the worst segment. To overcome a disparity in temporal resolution amongst the segments, a length (i.e., a view angle extent) φn of each segment n is selected so that, after weighting, temporal resolution of each segment is roughly the same. Thus, the example shown in FIG. 8 is changed to that of FIG. 9 by substantially increasing lengths φ1 and φ4 of the 1st and 4th segments, respectively, and decreasing lengths φ2 and φ3 of the 2nd and 3rd segments. In this manner, overall system temporal resolution is improved. In general, lengths φn of each segment will depend on a type of weighting function used.

Because multi-segmentation is potentially time-consuming, the methods and apparatus of the present invention are most advantageously applied after an initial screening. For example, scanner 10 is commanded to perform cardiac calcification scoring using conventional methodology, such as half-scan with EKG gating. Once a location is identified for further investigation, scanner 10 "zooms into" the site and performs multi-segmentation scanning.

In one embodiment, CT imaging system 10 is configured to perform the methods described herein. For example, an EKG signal from EKG machine 50 is provided as an input to computer 36. Computer 36 selects an appropriate gantry rotation speed based upon a measured interval between R-peaks. Computer 36 is also programmed to obtain segments at appropriate times during the cardiac cycle and to assemble the segments into an image in accordance with the methods of the present invention. Modifiable parameters, for example, a number of segments to obtain and assemble for each image, are entered via console 40. In one embodiment, default values of modifiable parameters are provided, for example, by a computation based upon a measured cardiac cycle, the number of slices CT imaging system 10 is configured to obtain during a scan, and an available range of gantry 12 rotation rates. In the apparatus embodiments described herein, CT imaging system 10 is "conventional" in that no special gantry 12, radiation source 14, or detector array 18 is required. Instead, software (or firmware) is provided to configure the system to obtain high temporal resolution for cardiac imaging, with only on input for a EKG signal required.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, as indicated above, a quiescent period of a cardiac cycle is selected in some embodiments as the most advantageous portion of a cycle for providing images with a minimum of motion-induced artifacts. However, a reduction of motion-induced imaging artifact is achieved by the methods of this invention irrespective of which portion of the cardiac cycle is selected. In addition, although projections covering an angular range of 180° plus a fan angle optimize temporal resolution by reducing data acquisition time to less than a full scan, the invention is equally applicable to full-scan configurations. Furthermore, schemes to make use of redundant samples in 360° sampling may be used in full-scan configurations. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims.

What is claimed is:

1. A method for imaging a heart with a scanning computed tomography (CT) imaging system, said method comprising the steps of:

measuring a cardiac cycle of a patient;

selecting view angle extents for a plurality of segments of data to equalize temporal resolution of the segments of data after a weighting function is applied;

scanning the patient's heart with the scanning CT imaging system at an angular rate asynchronous to the measured cardiac cycle to obtain image data, wherein the image data includes quiescent image data obtained at a first view angle during a first gantry rotation and quiescent image data obtained at a second view angle different than the first view angle during a second gantry rotation; and assembling an image of the patient's heart representative of a selected portion of the cardiac cycle from chronologically discontinuous segments of the image data.

2. A method in accordance with claim 1 wherein scanning the patient's heart comprises the step of axially scanning the patient's heart.

3. A method in accordance with claim 2 wherein the patient is supported on a moveable table, said step of axially scanning the patient's heart is repeated a plurality of times and said step of assembling an image of the patient's heart is repeated for each step of axially scanning the patient's heart, and further comprising the step of indexing the table between said steps of axially scanning the patient's heart.

4. A method in accordance with claim 3 wherein said step of indexing the table comprises the step of indexing the table so that consecutive scans from which images are assembled are of non-overlapping volumes.

5. A method in accordance with claim 3 wherein said step of indexing the table comprises the step of indexing the table an amount equal to a volume coverage of data in a preceding scan.

6. A method in accordance with claim 2 wherein assembling chronologically discontinuous segments of data comprises the step of assembling segments of data representative of a set of adjacent view angle ranges.

7. A method in accordance with claim 6 wherein assembling segments of data representative of a set of adjacent view angle ranges comprises the step of assembling segments of data having overlapping view angle ranges.

8. A method in accordance with claim 7 and further comprising the step of applying a blending weighting function to the segments of data.

9. A method in accordance with claim 7 and further comprising the step of applying an additional artifact-reducing weighting function to the blended, assembled segments of data.

10. A method in accordance with claim 6 wherein scanning the patient's heart comprises obtaining shuffled segments of data representative of a set of adjacent view angle ranges.

11. A method in accordance with claim 5 wherein assembling chronologically discontinuous segments of image data comprises the step of assembling a set of discontinuous segments comprising less than a full 360° of scanned data.

12. A method in accordance with claim 11 wherein the scanning CT imaging system comprises a radiation source emitting a fan-shaped beam and a detector detecting a fan angle of image data, and assembling a set of discontinuous segments comprising less than a full 360° of scanned data comprises the step assembling a set of discontinuous segments of data covering an angular range of 180° plus the fan angle.

13. A method in accordance with claim 1 wherein scanning the patient's heart comprises the step of helically scanning the patient's heart, wherein said helical scanning advances along a z-axis.

14. A method in accordance with claim 13, wherein:
the scanning CT imaging system is a multi-slice CT imaging system;

helically scanning the patient's heart comprises the step of scanning the patient's heart with the multi-slice CT imaging system to obtain a plurality of slices of image data; and assembling an image of the patient's heart comprises the step of assembling chronologically discontinuous segments of image data including image data from a plurality of slices into one planar slice representative of the selected portion of the cardiac cycle.

15. A method in accordance with claim 14 wherein assembling chronologically discontinuous segments of data comprises the step of assembling segments of data representative of a set of adjacent view angle ranges.

16. A method in accordance with claim 15 wherein assembling segments of data representative of a set of adjacent view angle ranges comprises the step of assembling segments of data having overlapping view angle ranges.

17. A method in accordance with claim 16 and further comprising the step of applying a blending weighting function to the segments of data.

18. A method in accordance with claim 16 and further comprising applying an additional artifact-reducing weighting function to the blended, assembled segments of data.

19. A method in accordance with claim 15 wherein scanning the patient's heart with the multi-slice CT imaging system to obtain a plurality of slices of image data comprises obtaining shuffled segments of data representative of a set of adjacent view angle ranges.

20. A method in accordance with claim 14 wherein assembling chronologically discontinuous segments of image data from a plurality of slices into one planar slice representative of the selected portion of the cardiac cycle comprises the step of assembling a set of discontinuous segments comprising less than a full 360° of scanned data.

21. A method in accordance with claim 20 wherein the scanning CT imaging system comprises a radiation source emitting a fan-shaped beam and a detector detecting a fan angle of image data, and assembling a set of discontinuous segments comprising less than a full 360° of scanned data comprises the step assembling a set of discontinuous segments of data covering an angular range of 180° plus the fan angle.

22. A method in accordance with claim 14 wherein helically scanning the patient's heart comprises the steps of:
selecting a number of segments to assemble in said assembling step; and
adjusting a scanning pitch so that a same slice location of the patient's heart is scanned a number of times equal to the selected number of segments.

23. A method in accordance with claim 14 wherein helically scanning the patient's heart comprises the steps of:
selecting a number of segments to assemble in said assembling step; and
adjusting a scanning pitch so that each segment starts at a same location on the z-axis.

24. A method in accordance with claim 14 wherein helically scanning the patient's heart comprises the steps of:
selecting a number of segments to assemble in said assembling step; and
adjusting a scanning pitch so that a z-axis location for neighboring views in adjacent segments has substantially the same z-axis location.

25. A scanning computed tomography (CT) imaging system for imaging a heart, said system configured to:
compute a cardiac cycle of a patient from an EKG signal;
select view angle extents for a plurality of segments of data to equalize temporal resolution of the segments of data after a weighting function is applied;

scan the patient's heart a plurality of times at a cycle rate asynchronous to the measured cardiac cycle to obtain image data, wherein the image data includes quiescent image data obtained at a first view angle during a first gantry rotation and quiescent image data obtained at a second view angle different than the first view angle during a second gantry rotation; and assemble an image of the patient's heart representative of a selected portion of the cardiac cycle from chronologically discontinuous segments of the image data.

26. A system in accordance with claim 25 further configured to axially scan the patient's heart.

27. A system in accordance with claim 26 further comprising a moveable table configured to support the patient, and wherein said system is further configured to perform plural axial scans of the patient's heart, to assemble an image of the patient's heart for each of said plural axial scans, and to index said table between each of said axial scans.

28. A system in accordance with claim 27 further configured to index said table so that consecutive scans from which images are assembled are of non-overlapping volumes.

29. A system in accordance with claim 27 further configured to index said table an amount equal to a volume coverage of data in a preceding scan.

30. A system in accordance with claim 26 wherein said system being configured to assemble chronologically discontinuous segments of data comprises said system being configured to assemble segments of data representative of a set of adjacent view angle ranges.

31. A system in accordance with claim 30 wherein said system being configured to assemble segments of data representative of a set of adjacent view angle ranges comprises said system being configured to assemble segments of data having overlapping view angle ranges.

32. A system in accordance with claim 31 further configured to apply a blending weighting function to said segments of data.

33. A system in accordance with claim 31 further configured to apply an additional artifact-reducing weighting function to blended, assembled segments of data.

34. A system in accordance with claim 30 wherein said system being configured to scan the patient's heart comprises said system being configured to obtain shuffled segments of data representative of a set of adjacent view angle ranges.

35. A system in accordance with claim 29 wherein said system being configured to assemble chronologically discontinuous segments of image data comprises said system being configured to assemble a set of discontinuous segments comprising less than a full 360° of scanned data.

36. A system in accordance with claim 35 further comprising a radiation source emitting a fan-shaped beam and a detector detecting a fan angle of image data, and said system being configured to assemble a set of discontinuous segments comprising less than a full 360° of scanned data comprises said system being configured to assemble a set of discontinuous segments of data covering an angular range of 180° plus the fan angle.

37. A system in accordance with claim 25 further configured to helically scan the patient's heart, and to advance said helical scanning along a z-axis.

38. A system in accordance with claim 37 further configured to helically scan the patient's heart to obtain a plurality of slices of image data; and said system being configured to assemble an image of the patient's heart comprises said system being configured to assemble chronologically discontinuous segments of image data including image data from a plurality of slices into one planar slice representative of the selected portion of the cardiac cycle.

39. A system in accordance with claim 38 wherein said system being configured to assemble chronologically discontinuous segments of data comprises said system being configured to assemble segments of data representative of a set of adjacent view angle ranges.

40. A system in accordance with claim 39 wherein said system being configured to assemble segments of data representative of a set of adjacent view angle ranges comprises said system being configured to assemble segments of data having overlapping view angle ranges.

41. A system in accordance with claim 40 further configured to apply a blending weighting function to the segments of data.

42. A system in accordance with claim 40 further configured to apply an additional artifact-reducing weighting function to the blended, assembled segments of data.

43. A system in accordance with claim 39 wherein said system being configured to scan the patient's heart with the multi-slice CT imaging system to obtain a plurality of slices of image data comprises said system being configured to obtain shuffled segments of data representative of a set of adjacent view angle ranges.

44. A system in accordance with claim 38 wherein said system being configured to assemble chronologically discontinuous segments of image data from a plurality of slices into one planar slice representative of the selected portion of the cardiac cycle comprises said system being configured to assemble a set of discontinuous segments comprising less than a full 360° of scanned data.

45. A system in accordance with claim 44 further comprising a radiation source emitting a fan-shaped beam and a detector detecting a fan angle of image data, and wherein said system being configured to assemble a set of discontinuous segments comprising less than a full 360° of scanned data comprises said system being configured to assemble a set of discontinuous segments of data covering an angular range of 180° plus the fan angle.

46. A system in accordance with claim 38 wherein said system being configured to helically scan the patient's heart includes:

said system being configured to select a number of segments to assemble in said assembling step; and to adjust a scanning pitch so that a same slice location of the patient's heart is scanned a number of times equal to the selected number of segments.

47. A system in accordance with claim 38 wherein said system being configured to helically scan the patient's heart includes:

said system being configured to select a number of segments to assemble in said assembling step; and to adjust a scanning pitch so that each segment starts at a same location on the z-axis.

48. A system in accordance with claim 38 wherein said system being configured to helically scan the patient's heart includes:

said system being configured to select a number of segments to assemble in said assembling step; and to adjust a scanning pitch so that a z-axis location for neighboring views in adjacent segments has substantially the same z-axis location.

49. A method for imaging a heart with a scanning computed tomography (CT) imaging system, said method comprising the steps of:

measuring a cardiac cycle of a patient;

scanning the patient's heart with the scanning CT imaging system at an angular rate asynchronous to the measured cardiac cycle to obtain image data, wherein the image data includes quiescent image data obtained at a first view angle during a first gantry rotation and quiescent image data obtained at a second view angle different than the first view angle during a second gantry rotation;

assembling a plurality of segments of data representative of a set of overlapping view angle ranges; and reconstructing an image of the patient's heart representative of a selected portion of the cardiac cycle from chronologically discontinuous segments of the image data.

50. A method for imaging a heart with a scanning computed tomography (CT) imaging system, said method comprising the steps of:

measuring a cardiac cycle of a patient;

scanning the patient's heart with the scanning CT imaging system at an angular rate of at least one of approximately 0.8 rotations per second when the heart beat is between approximately 60 and approximately 65 beats per minute, approximately 0.7 rotations per second when the heart beat is between approximately 65 and approximately 75 beats per minute, approximately 0.6 rotations per second when the heart beat is between approximately 70 and approximately 88 beats per minute, and approximately 0.5 rotations per second when the heart beat is between approximately 89 and approximately 100 beats per minute to collect image data, wherein the image data includes quiescent image data obtained at a first view angle during a first gantry rotation and quiescent image data obtained at a second view angle different than the first view angle during a second gantry rotation;

reconstructing an image of the patient's heart representative of a selected portion of the cardiac cycle from chronologically discontinuous segments of the image data.

* * * * *